United States Patent
Nakamura et al.

(10) Patent No.: US 7,081,562 B1
(45) Date of Patent: Jul. 25, 2006

(54) MODEL ANIMAL WITH FAVORITE ONSET OR RHEUMATOID ARTHRITIS

(75) Inventors: Akira Nakamura, Sendai (JP); Toshihiro Nukiwa, Sendai (JP); Toshiyuki Takai, Sendai (JP)

(73) Assignee: Japan Science and Technology Agency, Saitama (JP)

( * ) Notice: Subject to any disclaimer, the term of this patent is extended or adjusted under 35 U.S.C. 154(b) by 597 days.

(21) Appl. No.: 10/148,413

(22) PCT Filed: Jul. 26, 2000

(86) PCT No.: PCT/JP00/04976

§ 371 (c)(1),
(2), (4) Date: May 29, 2002

(87) PCT Pub. No.: WO01/47354

PCT Pub. Date: Jul. 5, 2001

(30) Foreign Application Priority Data

Dec. 28, 1999 (JP) ................................. 11-373366

(51) Int. Cl.
*A01K 67/027* (2006.01)
*C12N 15/00* (2006.01)

(52) U.S. Cl. .......................................... 800/18; 800/21
(58) Field of Classification Search .................. 800/13, 800/18, 21
See application file for complete search history.

(56) References Cited

OTHER PUBLICATIONS

Kleinau et al. (May 1, 2000) Induction and suppression of collagen-induced arthritis is dependent on distinct Fc(gamma) receptors. Journal of Experimental Medicine 191(9): 1611-1616.*
Campbell and Wilmut (1997) Totipotency or multipotentiality of cultured cells: Applications and progress. Theriogenology 47: 63-72.*
Doetschman, T. (1999) Interpretation of phenotype in genetically engineered mice. Laboratory Animal Science 49(2): 137-143.*
Donehower et al. (1995) Effects of genetic background on tumorigenesis in p53-deficient mice. Molecular Carcinogenesis 14: 16-22.*
Jacks et al. (1992) Effects of an Rb mutation in the mouse. Nature 359: 295-300.*
Jaenisch et al. (1988) Transgenic Animals. Science 240: 1468-1474.*
Kuehn et al. (1987) A potential animal model for Lesch-Nyhan syndrome through introduction of HPRT mutations into mice. Nature 326: 295-298.*
Moens et al. (1993) Defects in heart and lung development in compound heterozygotes for two different targeted mutations at the N-myc locus. Development 119: 485-499.*
Mullins et al. (1996) Transgenesis in the rat and larger mammals. J. Clin. Invest. 97(7): 1557-1560.*
Petridou et al. (2003) Heterogeneous inducible mammary-specific expression of JAB/SOCS1 in lactating transgenic mice is associated with no obvious phenotype, even at the cellular level. Transgenic Research 12: 693-706.*
Sigmund, CD (2000) Viewpoint: Are studies in genetically altered mice out of control? Arterioscler. Thromb. Vasc. Biol. 20: 1425-1429.*
Sandra Kleinau, et al., "Induction and Suppression of Collagen-induced Arthritis Is Dependent on Distinct Fcβ Receptors", Journal of Experimental Medicine, May 1, 2000, pp. 1611-1616, vol. 191, No. 9.
Takae Yuasa, et al., "Deletion of Fcβ Receptor IIB Renders H-2$^b$ Mice Susceptible to Collagen-induced Arthritis", Journal of Experimental Medicine, Jan. 4, 1999, pp. 187-194, vol. 189, No. 1.
Toshiyuki Takai, et al., "Augmented humoral and anaphylactic responses in FcγRII-deficient mice", Nature, Jan. 1996, pp. 346-349, vol. 379, No. 25.

(Continued)

*Primary Examiner*—Anne-Marie Falk
(74) *Attorney, Agent, or Firm*—Ann S. Hobbs; Venable LLP; Robert Kinberg

(57) ABSTRACT

The present invention provides a model animal with favorite onset of rheumatoid arthritis wherein the severity of arthritis reaches the maximum level and its onset ratio is a hundred percent, and a screening method of a remedy for rheumatoid arthritis by using the model animal. A mouse whose function of immunoglobulin Fcγ receptor IIB gene is deficient on its chromosome and a wild-type collagen-induced arthritis-susceptible DBA/1J mouse are backcrossed six times or more, and a model mouse with favorite onset of rheumatoid arthritis is constructed. This model mouse with favorite onset of rheumatoid arthritis is immunized with bovine joint-origin type II collagen to develop collagen-induced arthritis.

5 Claims, 1 Drawing Sheet

OTHER PUBLICATIONS

Linda K. Myers, et al., "Collagen-Induced Arthritis, An Animal Model Of Autoimmunity", Life Science, 1997, pp. 1861-1874, vol. 61, NO. 19.

Paul H. Wooley, et al., "Variations in Immunogenetic Regulation Provide Evidence for Multiple Arthritogenic Epitopes on the Collagen Molecule[1]", The Journal of Immunology, Oct. 1985, pp. 2443-2451, vol. 135, No. 4.

Raphael Clynes, et al., "Modulation of Immune Complex-induced Inflammation *In vivo* by the Coordinate Expression of Activation and Inhibitory Fc Receptors", Journal of Experimental Medicine, Jan. 4, 1999, pp. 179-185, vol. 189, No. 1.

Paul H. Wooley, et al., "Major Histocompatibility Complex (1 Region) Linkage and Antibody Correlates", Journal of Experimental Medicine, Sep. 1981, pp. 688-700, vol. 154, No. 3.

Mikael C.I. Karlsson, et al., "Efficient IgG-mediated suppression of primary antibody responses in Fcγ receptor-deficient mice", Proc. Natl. Acad. Sci., Mar. 2, 1999, pp. 2244-2249, vol. 96.

Sara Wernersson, et al., "IgG-Mediated Enhancement of Antibody Responses Is low in Fc Receptor γ Chain-Deficient Mice and Increased in FcγRII-Deficient Mice[1]", The Journal of Immunology, Jul. 15, 1999, pp. 618-622, vol. 163, No. 2.

Sebastian Amigorena, et al., "Cytoplasmic Domain Heterogeneity and Functions of IgG Fc Receptors in B Lymphocytes", Science, Jun. 26, 1992, pp. 1808-1812, vol. 256.

Wolf H. Fridman, et al., "Structural Bases of Fcγ Receptor Functions", Immunological Reviews, 1992, pp. 49-76, No. 125.

\* cited by examiner experimental progress (days after immunization)

experimental progress (days after immunization)

MODEL ANIMAL WITH FAVORITE ONSET OR RHEUMATOID ARTHRITIS

TECHNICAL FIELD

The present invention relates to a model rodent animal with favorite onset of rheumatoid arthritis, a screening method of onset promoting agents or onset suppressive agents, or onset feature promoting agents or onset feature suppressive agents of rheumatoid arthritis by using the model animal, and a pharmaceutical composition for prevention and improvement of diagnostic signs of rheumatoid arthritis.

PRIOR ART

It is known that immunoglobulin (Ig) is found in the body fluids of all vertebrate animals from fishes to mammals, and is produced by the lymphatic system cells. It is classified into five classes, namely, IgG, IgM, IgA, IgD, and IgE, according to the physicochemical properties and immunological properties, wherein the fundamental structure of molecules are common to each class, and is composed from H chain having fifty to seventy thousand molecular weight and L chain having twenty-three thousand molecular weight, and the H chain is structured with $\gamma$, $\mu$, $\alpha$, $\delta$, and $\epsilon$ chain corresponding to IgG, IgM, IgA, IgD, and IgE. The two H chains from the hinge region to the C terminal obtained by decomposing this Ig molecule with papain, which are bound by S—S ligation is called a Fc fragment, and the receptor on the cell surface which this Fc fragment binds to is called a Fc receptor (hereinafter "FcR"). Moreover, Fc receptors, receptor molecules for the antigen of T lymphocytes, major histocompatibility antigens, $\beta_2$ microglobulins, carcinoembryonic antigens, cell membrane proteins of lymphocytes or the like are known as molecules having the same structure as that of Ig (immunoglobulin superfamily).

The above-mentioned FcR exists on the surface of cells in such as the immune system and the like, and the Fc$\gamma$ receptor (hereinafter "Fc$\gamma$R") among them, which is a receptor protein that binds specifically to the $\gamma$ chain of IgG in the body fluid, is classified mainly into three types, type I (CD64 antigen), type II (CD32 antigen), and type I I (CD16 antigen), based on the similarity of gene structure. Among these, Fc$\gamma$RII differs from the other FcRs in that it has low affinity to the IgG of the monomer, binds to the polyvalent IgG that has become an immune complex, and is widely expressed in the hemopoietic stem cells including monocytes, macrophages, polymorphonuclear (PMN) leukocytes, mast cells, platelets, some of the T cell lymphocytes and B cell lymphocytes. Moreover, three types of receptors having different gene arrangements, Fc$\gamma$RIIA, Fc$\gamma$ RIIB, and Fc$\gamma$RIIC, exist in the Fc$\gamma$RII, and it is known that each of them are positioned in the 1q23 of a chromosome.

Unlike the other FcRs, the above-mentioned Fc$\gamma$RIIB does not associate with $\gamma$ chain, and has an amino acid sequence (ITIM: Immunoreceptor Tyrosine-based Inhibition Motif) which transmits suppressive signal to the intracellular domain (Immunol. Rev. 125, 49–76, 1992, Science 256, 1808–1812, 1992). In order to elucidate these physiological functions of Fc$\gamma$ RIIB, the inventors of the present invention had already constructed Fc$\gamma$RIIB knockout mice (Nature 379, 346–349, 1996), and constructed arthritis model mice which are generated by immunizing Fc$\gamma$RIIB knockout mice with type II collagen (J. Exp. Med. 189, 187–194, 1999). However, the onset feature of arthritis was the same as that of DBA/1J mice, and thus, they were not so useful.

On the other hand, collagen-induced arthritis (CIA) and adjuvant arthritis are known as animal models for chronic rheumatism and inflammation in humans. CIA is an arthritis which is induced by sensitizing rats with type II collagen, based on the knowledge that antibody for type II collagen exists very frequently in the serum and synovial fluid of the joint of patients with chronic rheumatism. Compared to adjuvant arthritis, it does not show mucocutaneous symptoms, is possible to induce to monkeys aside from mice and rats, indicates tendency of tolerance exacerbation, and is thereby known as a model animal much closer to rheumatoid arthritis. Moreover, there is a correlation between the onset of CIA and the MHC haplotype which the lineage of the animal being used has, wherein the onset ratio is high for mice having H-2q (DBA/1J mice), H-2r (RIIIS/J mice), and H-2d (BALB/c mice) haplotypes. DBA/1J mice with H-2q are frequently used, whereas for rats, Lewis, Wister, BB/DR and the like are very frequently used.

The analysis of CIA has progressed in mice with clear genetic background, and as mentioned above, H-2q (DBA/1J mice), H-2r (RIIIS/J mice), and H-2d (BALB/c mice) mice having haplotypes can induce arthritis as disease model mice. However, there were problems that the onset ratio was not a hundred percent and the severity of arthritis did not reach the maximum level. An object of the present invention is to provide a model animal of rheumatoid arthritis that is much better compared to the conventional CIA model animal, that is, a model animal with favorite onset of rheumatoid arthritis wherein the severity of rheumatoid arthritis reaches the maximum level and its onset ratio is a hundred percent, and a screening method of a remedy or the like for rheumatoid arthritis by using the model animal.

SUMMARY OF THE INVENTION

The inventors of the present invention have reported that CIA can be induced to Fc$\gamma$RIIB-deficient mice with haplotype H-2b, which has been said that onset of collagen-induced arthritis is generally not found, by immunizing with bovine joint-origin type II collagen (C-II) (J. Exp. Med. 189, 187–194, 1999). The anti-type II collagen antibody titer was high for said Fc$\gamma$RIIB-deficient mice, and its onset feature of arthritis was the same as that of wild-type DBA/1J mice. It was found that since the onset of CIA which is an autoimmune disease is bonded to MHC haplotype, said bonding is released by the deficiency of Fc$\gamma$RIIB. Consequently, it was discovered that the CIA which is developed by Fc$\gamma$IIB-deficient DBA/1J mice obtained by backcrossing DBA/1J mice for eight generations for a period of two and a half years, develop arthritis at an early stage compared to DBA/1J mice, and exacerbate the symptoms, and thus the present invention had been completed.

More specifically, the present invention relates to a model rodent animal with favorite onset of rheumatoid arthritis, wherein a rodent animal whose function of immunoglobulin Fc $\gamma$ receptor IIB gene is deficient on its chromosome and a wild-type collagen-induced arthritis-susceptible rodent animal of the same species as said rodent animal are backcrossed to obtain the model rodent animal, and onset of collagen-induced arthritis is found when immunized with type II collagen (claim 1); the model rodent animal with favorite onset of rheumatoid arthritis according to claim 1, wherein the model rodent animal with favorite onset of rheumatoid arthritis is a model mouse with favorite onset of rheumatoid arthritis or a model rat with favorite onset of rheumatoid arthritis (claim 2); the model rodent animal with favorite onset of rheumatoid arthritis according to claim 2, wherein a mouse whose function of immunoglobulin Fcγ receptor IIB gene is deficient on its chromosome and a wild-type DBA/1J mouse are backcrossed (claim 3); the model rodent animal with favorite onset of rheumatoid arthritis according to any of claims 1 to 3, wherein backcrossing is conducted six times or more (claim 4); and the model rodent animal with favorite onset of rheumatoid arthritis according to any of claims 1 to 4, wherein the type II collagen is a bovine joint-origin type II collagen (claim 5).

Furthermore, the present invention relates to a screening method of onset promoting agents or onset suppressive agents of rheumatoid arthritis, wherein the model rodent animal with favorite onset of rheumatoid arthritis according to any of claims 1 to 5 is immunized with type II collagen, test substances are administered to said rodent animal before, after or at the same time it is immunized, or after immunization when rheumatoid arthritis is not developed, and evaluation with the severity of onset of collagen-induced arthritis as an index is made (claim 6); the screening method of onset promoting agents or onset suppressive agents of rheumatoid arthritis according to claim 6, wherein a comparative evaluation with a wild-type collagen-induced arthritis-non-susceptible rodent animal and/or a wild-type collagen-induced arthritis-susceptible rodent animal used as a control is made when evaluating with the severity of the onset of collagen-induced arthritis as an index (claim 7); a screening method of onset feature promoting agents or onset feature suppressive agents of rheumatoid arthritis, wherein the model rodent animal with favorite onset of rheumatoid arthritis according to any of claims 1 to 5 is immunized with type II collagen, test substances are administered to said rodent animal after immunization when rheumatoid arthritis is developed, and evaluation with the severity of onset of collagen-induced arthritis as an index is made (claim 8); and the screening method of onset feature promoting agents or onset feature suppressive agents of rheumatoid arthritis according to claim 8, wherein a comparative evaluation with a wild-type collagen-induced arthritis-non-susceptible rodent animal and/or a wild-type collagen-induced arthritis-susceptible rodent animal used as a control is made when evaluating with the severity of the onset feature of collagen-induced arthritis as an index (claim 9).

Moreover, the present invention relates to an onset promoting agent of rheumatoid arthritis obtained by the screening method of onset promoting agents or onset suppressive agents of rheumatoid arthritis according to claim 6 or 7 (claim 10); an onset suppressive agent of rheumatoid arthritis obtained by the screening method of onset promoting agents or onset suppressive agents of rheumatoid arthritis according to claim 6 or 7 (claim 11); an onset feature promoting agent of rheumatoid arthritis obtained by the screening method of onset feature promoting agents or onset feature suppressive agents of rheumatoid arthritis according to claim 8 or 9 (claim 12); an onset feature suppressive agent of rheumatoid arthritis obtained by the screening method of onset feature promoting agents or onset feature suppressive agents of rheumatoid arthritis according to claim 8 or 9 (claim 13); a pharmaceutical composition that is a remedy used as a therapy for patients in need of an onset suppressive agent of rheumatoid arthritis, comprising the onset suppressive agent of rheumatoid arthritis according to claim 11 as an active substance (claim 14); and a pharmaceutical composition that is a remedy used as a therapy for patients in need of an onset feature suppressive agent of rheumatoid arthritis, comprising the onset feature suppressive agent of rheumatoid arthritis according to claim 13 as an active substance (claim 15).

BEST MODE FOR CARRYING OUT THE INVENTION

Figure 1:
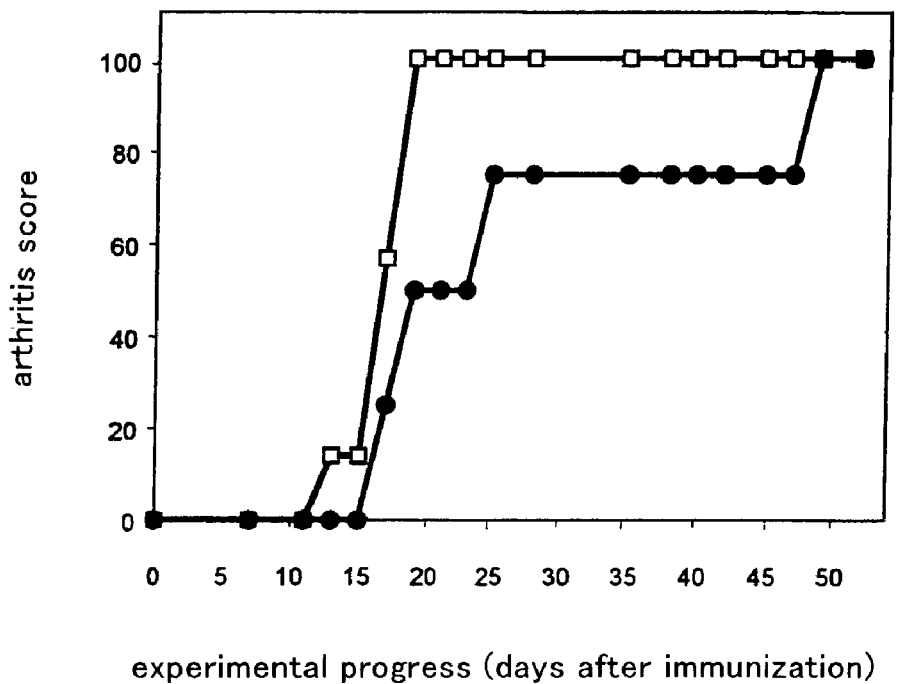
FIG. 1 is a graph indicating the results of onset ratio of arthritis of a model mouse with favorite onset of rheumatoid arthritis in the present invention and a DBA/1J mouse.
Figure 2:
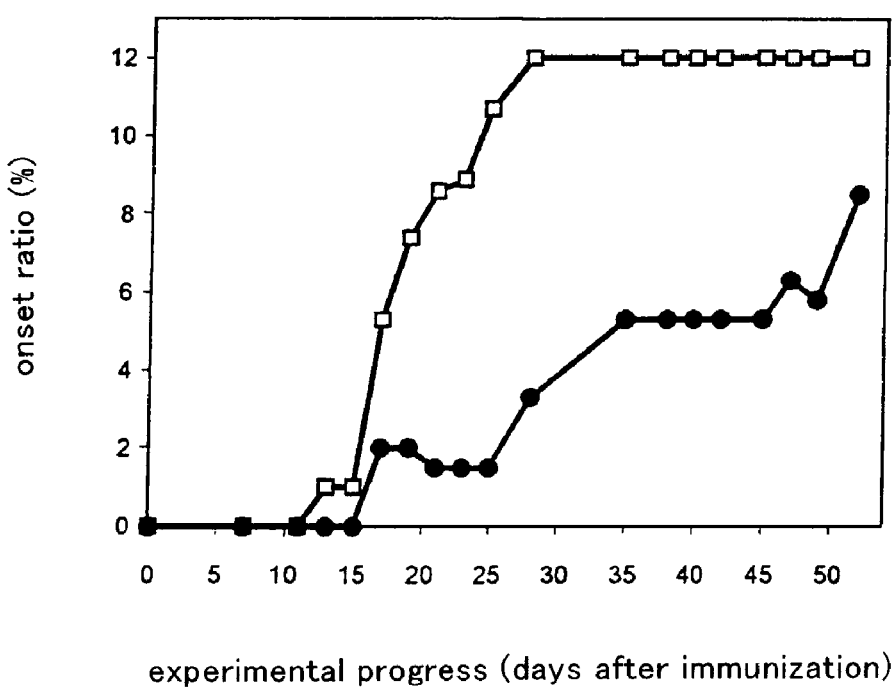
FIG. 2 is a graph indicating the results of arthritis score of a model mouse with favorite onset of rheumatoid arthritis in the present invention and a conventional DBA/1J mouse.

In the present invention, a "rodent animal whose function of immunoglobulin Fcγ receptor IIB (FcγIIB) gene is deficient on its chromosome" means a rodent animal such as a mouse, a rat or the like, whose function of expressing FcγRIIB is impaired by inactivation of endogenous genes of the rodent animal encoding FcγRIIB caused by genetic mutation such as destruction, deficiency, substitution or the like. Moreover, in the present invention, a "wild-type collagen-induced arthritis (CIA)-susceptible rodent animal of the same species as said rodent animal" means a rodent animal such as a mouse, a rat or the like, which has a MHC haplotype that develops CIA. Specific examples of mice are DBA/1J mice, RIIIS/J mice, BALB/c mice and the like, and examples of rats are Lewis rats, Wister rats, BB/DR rats and the like. Particularly, using mice of a DBA/1J-lineage is preferable, since said mice are mice that develop collagen-induced arthritis at a high ratio, and backcrossing to mice of this lineage can further increase the onset ratio. In addition, in the present invention, a "model rodent animal with favorite onset of rheumatoid arthritis" means a rodent animal such as a mouse, a rat or the like, wherein at least a high onset ratio of CIA and large severity of onset exacerbation are found when immunized with the use of type II collagen, compared to the above-mentioned wild-type CIA-susceptible rodent animal. Now, the constructing method of a rodent animal whose function of FcγRIIB gene is deficient on its chromosome will be explained, by giving FcγRIIB knockout mouse as an example.

A mouse whose function of FcγRIIB gene is deficient on its chromosome, namely, the FcγRIIB knockout mouse, can be constructed by using the method as previously described (Nature, 379, 346–349, 1996) by the present inventors, or the like. Specifically, a gene fragment obtained from a mouse genomic library by using methods such as PCR or the like was used to screen the FcγRIIB gene, and the FcγRIIB gene which had been screened was subcloned by using a viral vector or the like, and was determined by DNA sequencing. A fragment that includes $S_2$ exon and $EC_1$ exon of said clone was substituted with pMC1 neo gene cassette or the like, and a target vector was prepared. This linearized vector was introduced into ES cells by methods such as electroporation or the like, followed by homologous recombination, and ES cells indicating resistance to G418 and the like were selected from said homologous recombinants. The clone of said cells were microinjected into the blastocysts of the mice, said blastocysts were returned to the tentative parent mice, and chimeric mice were generated. These chimeric mice were intercrossed with wild-type mice to obtain heterozygous mice, and these heterozygous mice were intercrossed to obtain FcγRIIB knockout mice.

The model rodent animal with favorite onset of rheumatoid arthritis in the present invention can be obtained by backcrossing the above-mentioned rodent animal whose function of FcγRIIB gene is deficient on its chromosome to the previously described wild-type CIA-susceptible rodent animal of the same species as said rodent animal, in the usual manner. Normally, it is necessary to backcross twelve generations or further for a congenic-lineage (DBA/1J-lineage). However, when backcrossing in the present invention, it is preferable to backcross multiple times, particularly, six times or more, from the point of the onset ratio of CIA and the severity of onset exacerbation. It is also preferable to backcross eight times or more in that it can further obtain a uniform experimental result. Backcrossing multiple times can be conducted by the following method: a first filial generation ($F_1$) from a rodent animal whose function of FcγRIIB gene is deficient on its chromosome and the previously mentioned wild-type CIA-susceptible rodent animal (DBA/1J mouse, for example) of the same species as said rodent animal (FcγRIIB knockout mouse, for example), and the above-mentioned wild-type CIA-susceptible rodent animal were bred; a second filial generation ($F_2$) obtained therefrom and the above-mentioned wild-type CIA-susceptible rodent animal were bred again; followed by repetition of said breeding. In the present invention, backcrossing six times, for example, means a rodent animal whose function of FcγRIIB gene is deficient on its chromosome, which is obtained by breeding between sixth filial generations ($F_6$).

The model rodent animal with favorite onset of rheumatoid arthritis in the present invention develops CIA by immunization with a method publicly known, by using type II collagen. However, it is preferable for the CIA onset ratio to be high and the severity of the onset exacerbation to be large, when compared to a wild-type CIA-susceptible rodent animal. Moreover, there is no particular limitation to the type II collagen used to develop CIA to the model rodent animal with favorite onset of rheumatoid arthritis in the present invention, and type II collagen that are commercially available such as bovine joint-origin type II collagen, chick joint-origin type II collagen, human serum-origin type II collagen, human joint synovial fluid-origin type II collagen and the like can be used. However, as to a model mouse with favorite onset of rheumatoid arthritis, it is preferable to use a bovine joint-origin type II collagen. In addition, as long as CIA can be induced to the model rodent animal with favorite onset of rheumatoid arthritis in the present invention, peptides including a part of the amino acid sequence of type II collagen or one wherein a part of the amino acid sequence had been mutated can also be used as an immunogen.

The screening method of onset promoting agents or onset suppressive agents of rheumatoid arthritis in the present invention is characterized in that a model rodent animal with favorite onset of rheumatoid arthritis is immunized with type II collagen, test substances are administered to said rodent animal before, after, or at the same time it is immunized, or after immunization when rheumatoid arthritis is not developed, and evaluation with the severity of the onset of collagen-induced arthritis as an index is made. Moreover, the screening method of onset feature promoting agents or onset feature suppressive agents of rheumatoid arthritis in the present invention is characterized in that a model rodent animal with favorite onset of rheumatoid arthritis is immunized with type II collagen, test substances are administered to said rodent animal after immunization when rheumatoid arthritis is developed, and evaluation with the severity of the onset feature of collagen-induced arthritis as an index is made.

There is no particular limitation to the administration method of test substances in the above-mentioned screening method, as long as it is an administration method that is publicly known, such as oral administration, intravenous injection, intramuscular injection or the like. In addition, as a method for evaluating with the severity of the onset of collagen-induced arthritis as an index, methods for evaluation of rheumatoid arthritis that are publicly known can be used, such as the date of outbreak, incidence, severity of outbreak or the like, of the swelling of knuckle joint or the like. As a method for evaluating with the severity of the onset feature of collagen-induced arthritis as an index, it can be conducted by observation of the severity of the improvement of diagnosis such as the swelling of knuckle joint or the like that had developed. When making these evaluations, it is preferable to perform a comparative evaluation of a wild-type collagen-induced arthritis-non-susceptible rodent animal and a wild-type collagen-induced arthritis-susceptible rodent animal used as controls.

The onset promoting agent of rheumatoid arthritis and onset feature promoting agent of rheumatoid arthritis that can be obtained by these screening methods are useful when elucidating the mechanism of the onset of CIA. Moreover, the onset suppressive agent of rheumatoid arthritis and onset feature suppressive agent of rheumatoid arthritis are useful as a remedy used as therapy for patients in need of an onset suppressive agent of rheumatoid arthritis and onset feature suppressive agent of rheumatoid arthritis, that is, an agent for prevention and/or diagnosis improvement of chronic rheumatism. Furthermore, there is a possibility that the onset suppressive agent of rheumatoid arthritis and the onset feature suppressive agent of rheumatoid arthritis can be used as a surgical treatment for rheumatoid arthritis.

The present invention will now be explained more specifically with the following examples, however, the technical scope of the invention is not limited to these examples.

Reference (Generation of FcγRIIB-Deficient Mice)

A genomic DNA clone for FcγRIIB gene was isolated by screening a 129/Sv/J (H-2b) mouse genomic DNA library. A targeting vector was constructed by replacing a 2.65 Kb fragment which includes two separate exons of $S_2$ and $EC_1$ of said clone to a pMC1 neo gene cassette (Toyobo Co., Ltd.). This linearized vector was introduced into ES cells (J1) by electroporation, and was homologously recombined.

The ES clone was isolated from the ES cells that were homologously recombined as mentioned above, a neomycin-resistant ES clone was screened to G418 and GANC (ganciclovir), and homologous recombinants were identified by Southern blotting. Genomic DNA isolated from the identified homologous recombinants was digested with Hind III, and the existence of targeting allele containing pMC1 neo gene cassette was confirmed. The said confirmed ES clone was microinjected into the blastocysts to generate chimeric mice, and the mice that had been generated were intercrossed with wild-type C57BL/6 (H-2b) mice to obtain heterozygous mice, then these heterozygous mice were intercrossed to obtain homozygous mice, and defective mice whose FcγRIIB gene is deficient on its chromosome were generated.

Example 1

Generation of Model Mice with Favorite Onset of Rheumatoid Arthritis

FcγIIB$^{-/-}$ (deficient) DBA/1J mice having haplotype H-2q were generated in the following manner: FcγIIB-deficient male mice obtained by the method of Reference 1 were intercrossed with DBA/1J female mice having H-2q, FcγIIB$^{+/-}$ DBA/1J mice ($F_1$) having haplotype H-2q thus obtained were intercrossed again with DBA/1J mice, FcγIIB$^{+/-}$ DBA/1J mice (F$_2$) having haplotype H-2q thus obtained were intercrossed again with DBA/1J mice, and this intercrossing was repeated further for eight times in the same manner. Intercrossing between the mice that had been backcrossed eight times thus obtained (Fc γIIB$^{+/-}$DBA/1J mice with haplotype H-2q) was conducted, and Fc γIIB$^{-/-}$ (deficient) DBA/1J mice were generated.

Example 2

Generation of an Adjuvant

A type II collagen prepared from bovine joint (Collagen Gijutsu-kenshukai) was dissolved in a solution (pH 8.0) wherein 0.15 M NaOH solution was added to 0.02 M HCL solution, to a final concentration of 4.0 mg/ml, to generate type II collagen solution. Two types of oil emulsions were generated by mixing 4.0 mg/ml of said type II collagen and 4.0 mg/ml of complete Freund's adjuvant (CFA) comprised of liquid paraffin, surface-active agent, and dead *Mycobacterium tuberculosis* in a connected syringe, and by mixing 4.0 mg/ml type II collagen (pH 8.0) and 4.0 mg/ml incomplete Freund's adjuvant (IFA) comprised of liquid paraffin and surface-active agent in a connected syringe.

Example 3

Onset of CIA Using Model Mice with Favorite Onset of Rheumatoid Arthritis

The FcγIIB-deficient DBA/1J mice (eight weeks of age: gender at randomly chosen) generated from the method described in the above-mentioned Example 1 were anesthetized by ether and its tail base were shaved, and 100 μl emulsion containing 200 μg each of type II collagen and CFA were subcutaneously injected to the mice for primary immunization. After the primary immunization, on day 21 and 42, 100 μl emulsion containing 200 μg each of type II collagen and IFA were subcutaneously injected and immunized, lead the model mice with favorite onset of rheumatoid arthritis to develop CIA, and evaluation of rheumatoid arthritis was conducted in the following manner.

Example 4

Onset Ratio and Arthritis Score of Arthritis

The evaluation of arthritis of mice with onset of CIA was conducted by grading each paw according to the following scoring system: no change, 0; swelling in one knuckle joint, 1; swelling in more than two knuckle joints, 2; swelling found in all joints, 3; and a maximum score of 12. In addition, DBA/1J mice were used as a control. As can be seen in FIG. 1, as to the DBA/1J mice used as a control (●:n=5), the onset ratio of arthritis for the initial immunization was 40 percent, and the day of outbreak was 23.3±4.6 days. Moreover, the arthritis score was 8.5 in average even after third immunization and did not reach the maximum level. On the other hand, as to the Fcγ IIB-deficient DBA/1J mice (□:n=12), onset of arthritis was found in all cases only by initial immunization, the day of outbreak was fast as 17.1±1.9 days, and the arthritis score after second immunization reached the perfect score of 12 for all cases. From these results, it was discovered that Fcγ IIB-deficient DBA/1J mice are efficient arthritis model mice wherein the onset ratio and arthritis score are high, compared to the DBA/1J mice that have been generally used for CIA (collagen-induced arthritis) hitherto.

INDUSTRIAL APPLICABILITY

According to the present invention, when immunized with type II collagen, a model rodent animal with favorite onset of rheumatoid arthritis wherein the severity of rheumatoid arthritis reaches the maximum level and its onset ratio is a hundred percent can be obtained. Therefore, using said model rodent animal with favorite onset of rheumatoid arthritis in the present invention enables further effective development of sovereign remedy for rheumatism and development of therapy, compared to the cases wherein a conventional model mouse or rat with favorite onset of rheumatoid arthritis are used.

What is claimed is:

1. A mouse model with favorite onset of rheumatoid arthritis, obtained by
   (i) crossing a first mouse strain, having an inactivation of its endogenous immunoglobulin Fcγ receptor IIB gene, with a second mouse strain, wherein said second mouse strain is a wild-type collagen-induced arthritis-susceptible mouse strain, to obtain a mouse having a heterozygous inactivation of its endogenous immunoglobulin Fcγ receptor IIB gene, and
   (ii) performing one or more backcrosses, wherein the first backcross is carried out by breeding the heterozygous mouse obtained in step (i) with said second mouse strain to obtain a mouse having a heterozygous inactivation of its endogenous immunoglobulin Fcγ receptor IIB gene, and
   (iii) intercrossing the heterozygous mice obtained in the last backcross of the one or more backcrosses to produce a mouse having a homozygous inactivation of its endogenous immunoglobulin Fcγ receptor IIB gene, wherein onset of collagen-induced arthritis is observed when said mouse having a homozygous inactivation of its endogenous immunoglobulin Fcγ receptor IIB gene is immunized with type II collagen, thereby producing a mouse model with favorite onset of rheumatoid arthritis.

2. The model mouse with favorite onset of rheumatoid arthritis according to claim 1, wherein said second mouse strain is a wild-type DBA/1J mouse.

3. The model mouse with favorite onset of rheumatoid arthritis according to claim 1 or 2, wherein backcrossing is conducted eight times or more.

4. The model mouse with favorite onset of rheumatoid arthritis according to claim 1 or 2, wherein the type II collagen is a bovine joint-origin type II collagen.

5. The model mouse with favorite onset of rheumatoid arthritis according to claim 3, wherein the type II collagen is a bovine joint-origin type II collagen.

* * * * *

UNITED STATES PATENT AND TRADEMARK OFFICE
CERTIFICATE OF CORRECTION

| | |
|---|---|
| PATENT NO. | : 7,081,562 B1 |
| APPLICATION NO. | : 10/148413 |
| DATED | : July 25, 2006 |
| INVENTOR(S) | : Nakamura et al. |

It is certified that error appears in the above-identified patent and that said Letters Patent is hereby corrected as shown below:

ON THE TITLE PAGE:

At column 1, line Item (54), correct the title to read as follows --MODEL ANIMAL WITH FAVORITE ONSET OF RHEUMATOID ARTHRITIS--.

IN THE SPECIFICATIONS:

At column 1, line 2, change "OR" to --OF--.

Signed and Sealed this

Twenty-sixth Day of December, 2006

JON W. DUDAS
*Director of the United States Patent and Trademark Office*